US005475612A

United States Patent [19]
Espinosa et al.

[11] Patent Number: 5,475,612
[45] Date of Patent: Dec. 12, 1995

[54] METHOD FOR THE DIRECT DETERMINATION OF PHYSICAL PROPERTIES OF HYDROCARBON PRODUCTS

[75] Inventors: Alain Espinosa; Didier C. Lambert, both of Lavera; Andre Martens, Chateauneuf les Martigues, all of France; Antoine Pasquier, London, England; Gilbert Ventron, Lavera, France

[73] Assignee: BP Oil International Limited, London, United Kingdom

[21] Appl. No.: 206,250

[22] Filed: Mar. 4, 1994

Related U.S. Application Data

[63] Continuation of Ser. No. 99,764, Jul. 30, 1993, abandoned, which is a continuation of Ser. No. 827,860, Jan. 30, 1992, abandoned, which is a continuation of Ser. No. 549,656, Jul. 9, 1990, abandoned, which is a continuation of Ser. No. 233,189, Aug. 17, 1988, abandoned.

[30] Foreign Application Priority Data

| Aug. 18, 1987 | [FR] | France | 87 11679 |
| Jun. 1, 1988 | [FR] | France | 88 07304 |
| Jun. 1, 1988 | [FR] | France | 88 07305 |

[51] Int. Cl.$^6$ .............................. G01J 3/42; G01N 33/22
[52] U.S. Cl. ...................... 364/500; 364/499; 250/339.07
[58] Field of Search ..................... 364/502, 497, 364/498, 499; 324/307, 310, 312; 356/300, 303, 326; 382/17; 250/226, 339.07, 339.08, 339.09, 339.12

[56] References Cited

U.S. PATENT DOCUMENTS

| 3,121,677 | 2/1964 | Coggeshall et al. | 208/178 |
| 3,666,932 | 5/1972 | White | 235/151.12 |
| 3,693,071 | 9/1972 | Dolbear | 324/0.5 R |
| 3,896,312 | 7/1975 | Brown et al. | 250/343 |
| 4,236,076 | 11/1980 | Judge et al. | 250/347 |
| 4,251,870 | 2/1981 | Jaffe | 364/500 |
| 4,267,572 | 5/1981 | Witte | 364/498 |
| 4,286,327 | 8/1981 | Rosenthal et al. | 364/498 |
| 4,318,616 | 3/1982 | Chamran et al. | 364/498 |
| 4,323,309 | 4/1982 | Akitomo et al. | 364/498 |
| 4,359,668 | 11/1982 | Schwartz et al. | 364/497 |
| 4,397,958 | 8/1983 | Vroom | 364/497 |
| 4,568,186 | 2/1986 | Yoshimura et al. | 364/498 |
| 4,642,778 | 2/1987 | Hieftje et al. | 364/498 |
| 4,660,151 | 4/1987 | Chipman et al. | 364/498 |
| 4,701,838 | 10/1987 | Swinkels et al. | 364/164 |
| 4,766,551 | 8/1988 | Begley | 364/498 |
| 4,800,279 | 1/1989 | Hieftje et al. | 250/339 |
| 5,397,899 | 3/1995 | DiFoggio et al. | 250/339.09 |
| 5,412,581 | 5/1995 | Tackett | 364/498 |
| 5,430,295 | 7/1995 | Le Febre et al. | 250/340 |

FOREIGN PATENT DOCUMENTS 8404594  5/1983  WIPO.

OTHER PUBLICATIONS

"Etude de la mesure en ligne de l'indice d'octane" by G. Goma et al from MESURES, vol. 33, No. 6/7, Jun.–Jul. 1968, pp. 96–99, Paris.
"Near–Infrared Reflectance Spectrometry: Tip of the Iceberg" from Analytical Chemistry, vol. 56, No. 8, Jul. 1984.
"Trends in Near–Infrared Analysis" by Buchanan et al from Trend in Analytical Chemistry, vol. 5, No. 6, 1986.
Kelly et al., Analytical Chemistry, (1989), 61, 313–320, "Prediction of Gasoline Octane Numbers etc.".
Jones et al., Chemical Engineering, Oct. 9, 1978, pp. 111–114, "Near Infrared Analyzers Refine Process Control".
Jones, Instrument Society Bulletin No. 0–87644–687–9, (1982), pp. 21–25 "Near–Infrared Analysis In The Process Industry".
Murrill, Instrument Society of America, (1981), pp. 12–15 "Fundamental of Process Control Theory".
Callis et al., Analytical Chemistry, (59), No. 9, May 1, 1987, "Process Analytical Chemistry" pp. 624A–626A, 628A, 630A, 632 A, 635A, 637A.
Callis, Abstract submitted for Lecture, Aug. 8, 1986.
Illman et al., Abstract submitted for Workshop, Sep. 1, 1986.
Callis, Lecture Notice, Sep. 22, 1986.
Callis, Abstract submitted for Lecture, Sep. 24, 1986.
Callis, Abstract for Lecture, Nov. 5–Jul. 1986.
Callis, Abstract for Paper in Analytical Chemistry.
Avery et al, "Infra–red Spectra of Hydrocarbons. II Analysis of Octane Mixtures by the Use of Infra–red Spectra obtained at Low Temperatures", J. Applied Physics, vol. 18, Nov. 1947, pp. 960–967.
Healy et al, "A New Approach to Blending Octanes", API Division of Refining, 24th mid–year meeting (New York City, Division of Refining 27 May 1959, vol. 39 III, 1959, 132–192).
Article: "New Method may Determine Octane Ratings of Gasoline Quicker, Better", Hydrocarbon Processing, Jul.

(List continued on next page.)

*Primary Examiner*—Michael Zanelli
*Attorney, Agent, or Firm*—Brooks Haidt Haffner & Delahunty

[57] ABSTRACT

The properties of a liquid hydrocarbon blend are determined from the NIR (Near Infra Red) spectrum of the components of the blend. This is accomplished by: (a) determining with an IR spectrometer, the absorbance of the components of the blend at a certain number of frequencies in the spectral range 16667 to 3840 cm$^{-1}$ starting from a defined base line, (b) determining for each component and each property, a spectral mixture index (SMI) by applying a correlation between the SMI and the absorbance values, and then (c) calculating the property (J) to be determined by applying a linear expression, $J = f_a SMI_a{}^J + f_s SMI_b{}^J + f_c SMI_c{}^J + \ldots f_o SMI_o{}^J$ where $SMI^J{}_{(a, b, c \ldots)}$ is the Spectral Mixture Index for property J for each component (a, b, c . . . ) and $f_{(a, b, c \ldots)}$ is the fraction by volume of that component in the final blend. The correlation in (b) is determined experimentally by multivariate regression, and is dependent upon the type of spectrometer used, the property to be determined, and the frequencies used.

18 Claims, No Drawings

OTHER PUBLICATIONS 1987, p. 19.

Hibbard et al, "Carbon–Hydrogen Groups in Hydrocarbons", Analytical Chemistry, vol. 21, No. 4, pp. 486–492 (Apr. 1949).

Stark et al, "Near–Infrared Analysis (NIRA): A Technology for Quantitative and Qualitative Analysis", Applied Spectroscopy Reviews, 22(4), pp. 335–339 (1986).

Weyer, "Near–Infrared Spectroscopy of Organic Substances", Applied Spectroscopy Reviews, 21 (1&2), 1–43 (1985).

Honigs, D. E., "Near–Infrared Analysis", Analytical Instrumentation, 14(1), 1–62 (1985).

Schoen et al, "Calculating Gasoline Blend Octane Ratings", Industrial and Engineering Chemistry, vol. 49, No. 9. pp. 1740–1742, Sep. (1985).

Gary et al, Petroleum Refining, 2nd edition, Marcel Dekker, New York, 1984.

Myers et al, "Determination of Gasoline Octane Numbers from Chemical Composition" Analytical Chemistry, vol. 47, No. 13, pp. 2301–2304, Nov. 1975.

Honigs et al, "Near–Infrared Determination of Several Physical Properties of Hydrocarbons", Analytical Chemistry, vol. 57, No. 2, Feb. 1985, pp. 443–445.

Whetsel, K. B. "Near Infrared Spectrophotometry". Applied Spectroscopy Reviews, 2(1), 1– 67) (1968).

Honigs et al, "Near–Infrared Reflectance Analysis by Gauss–Jordan Linear Algebra", Applied Spectroscopy, vol. 37, No. 6, 1983, pp. 491–497.

Borisevich et al, "Instrumentation and Automation Equipment Method for Determining Group Hydrocarbon Composition and the Octane Number of Reforming Gasolines with IR Spectroscopy for Purposes of Operation Control"; *Avtomatizatsiya* 1981, No. 3, pp. 13–15.

Dornheim et al, "Optimum Non–Linear Gasoline Blending", The Oil ansd Gas Journal, May 26, 1958.

METHOD FOR THE DIRECT DETERMINATION OF PHYSICAL PROPERTIES OF HYDROCARBON PRODUCTS

This application is a continuation of application Ser. No. 08/099,764 filed Jul. 30, 1993, which is a continuation of application Ser. No. 07/827,860 filed Jan. 30, 1992, which is a continuation of Ser. No. 07/549,656 filed Jul. 9, 1990, which is a continuation of Ser. No. 07/233,189 filed Aug. 17, 1988, all abandoned.

This invention relates to a method for the determination of physical properties of hydrocarbon products, particularly non-additive properties of blends of petroleum fractions, by carrying out NIR (near infra-red) spectroscopic analyses of the components of the blend and correlating these with the physical properties of the blend.

Callis et al, Analytical Chemistry, vol 59, no. 9, pp 624A–636A (May 1987) mention the possibility of determining the octane rating of an unleaded gasoline by NIR spectroscopy and point out, in this particular case, the existence of a connection between other properties of the products and the NIR spectra of the products.

However, when a product is produced by blending various components, which are often themselves mixtures, major problems are encountered in predicting the properties of the final blend. This arises from the fact that several properties do not follow the linear law of mixtures obeyed by the majority.

For example, in gasolines, octane numbers do not obey the linear law; in diesel oils, cloud point, flash point, pour point, cetane index, filterability, etc., do not obey; and in fuel oils, viscosity, density, etc, do not obey.

Blend tables have been drawn up, but this is a lengthy and laborious procedure in which it is difficult, if not impossible, to cover all possible combinations.

In practice, formulating such blends is associated with the problem of controlling the properties of the final blend, which usually must meet stringent specifications, because of the variability of the components of the blend. This applies particularly when the components originate from oil refinery processing units.

It is an object of the present invention to eliminate the above disadvantages and in particular to render unnecessary the use of blend tables by providing a method which enables the properties of a simple or complex mixture to be predicted by determinations carried out solely on the components of the blend.

Thus, according to the present invention there is provided a method for the determination of physical properties of a liquid hydrocarbon blend which method comprises the following steps:

(a) determining with an IR spectrometer, the absorbance at a certain number of frequencies in the spectral range 16667 to 3840 cm$^{-1}$ (0.6 to 2.6 microns), preferably 12500 to 3840 cm$^{-1}$, (0.8 to 2.6 microns), most preferably 4760 to 4000 cm$^{-1}$ (2.1 to 2.5 microns) for the components or arbitrary mixtures, starting from a defined base line, preferably corresponding to zero absorbance, (b) determining for each component I and each property J, a spectral mixture index $SMI^J_I$, by applying a correlation with the measured absorbance values, this correlation being determined experimentally by multivariate regression, depending on the type of spectrometer used, the property desired, and the frequencies used, (c) calculating the desired property sought, by applying a linear expression, $$J = f_a \, S_m \, I^J_a + f_b \, SMI^J_b + f_c \, SMI^J_c \ldots + f_o \, SMI^J_o \qquad (1)$$

each term of which is the product of the spectral mixture index of a component of the desired property and the fraction by volume of the component in the final blend.

The SMI of a component can be determined directly from absorbance values obtained for this component alone by applying the correlation mentioned above. However, the SMI of a component is preferably determined in an arbitrary mixture of a fraction of this component in a matrix by obtaining the near IR spectra of the matrix and of this mixture respectively, calculating the theoretical absorbance at each of the frequencies chosen, by applying a linear formula as a function of the absorbances of the matrix and the mixture at the same frequency, and calculating the $SMI^J$ of this component by applying the above correlation to the theoretical absorbances of the component.

If necessary, the correlative expression above contains linear, quadratic and homographic (i.e. ratio) terms.

The frequencies used are preferably chosen from the following 16:

4670 cm$^{-1}$
4640 cm$^{-1}$
4615 cm$^{-1}$
4585 cm$^{-1}$
4485 cm$^{-1}$
4405 cm$^{-1}$
4385 cm$^{-1}$
4332 cm$^{-1}$
4305 cm$^{-1}$
4260 cm$^{-1}$
4210 cm$^{-1}$
4170 cm$^{-1}$
4135 cm$^{-1}$
4100 cm$^{-1}$
4060 cm$^{-1}$
4040 cm$^{-1}$

The corresponding frequency expressed in statutory units (Hz) are obtained by multiplying these values by $3 \times 10^{10}$—the velocity of light in cm/s.

The spectrometer may be linked to a signal processing device to permit numerical treatment of the spectrum, preferably by Fourier transformation. The spectrometer suitably has a resolution power of 4 cm$^{-1}$.

Using the classic method, the absorbance, i.e. the logarithm of the attenuation ratio between the incident ray and the ray after passing through the product, is determined for each frequency.

This choice is neither exhaustive nor exclusive. The choice of other frequencies will not alter the method but will require the use of other coefficients in the models enabling the calculation of the desired properties from these spectra.

The time taken for analysis and processing of the data is less than 1 minute.

The base line (regarded as corresponding to zero absorbance) is suitably taken at 4780 cm$^{-1}$.

The blending equipment may be computer controlled by a feed-back control system for altering blending conditions in response to variations in the property of the product from the desired value, from the determination of the NIR spectra of the components.

The spectrometer used gives the absorbance measurements for the frequencies selected, and the values sought are obtained directly by multivariate regression.

Suitable products, the properties of which are to be determined, include motor spirit, diesel oil and fuel oil.

In the case of a motor spirit, the desired properties may include the research octane number (RON), the motor octane number (MON), clear or leaded, at different tetraethyl lead or tetramethyl lead contents, the density, the vapour pressure and distillation characteristics.

In this case the preferred frequencies may be reduced to seven, and are:

4670 cm$^{-1}$ 4485 cm$^{-1}$ 4332 cm$^{-1}$ 4305 cm$^{-1}$ 4210 cm$^{-1}$ 4100 cm$^{-1}$ 4060 cm$^{-1}$

In the case of a diesel oil, the properties may include cloud point, pour point, filterability, cetane index, distillation properties, flash point and viscosity.

The diesel oil may be of the type used for automotive or marine diesel engines, speciality gas oils, heating oils, fuel oils for low capacity boilers, etc. The oil which is the final product may be formulated from multiple hydrocarbon-containing basestocks selected from the following non-exhaustive list: naphtha, gasoline and gas oil. These components may be obtained from atmospheric or vacuum distillation units, from hydrocrackers or hydrotreatment units or from thermal or catalytic crackers. Additives may also be added, e.g. nitrates for improving the cetane index.

In the case of a fuel oil, the properties may be density, viscosity, thermal stability, distillation properties, flash point, etc.

Again, the final product may be formulated from multiple hydrocarbon-containing basestocks. These may include atmospheric or vacuum distillation residues, visbreaker residues, catalytic cracker or steam cracker residues and gas oils.

To obtain the required property of the product P, a spectral analysis of the mixture can be carried out, i.e. the absorbance values or optical densities $D_i$, corresponding to the frequencies $F_i$ can be measured, and the property required J can then be calculated using an expression of the following type:

$$J = C + \sum_{1}^{n} p_i D_i + \sum_{1}^{n} q_{ij} D_i \cdot D_j + \sum_{1}^{n} r_{ij} D_i/D_j \quad (2)$$

in which a constant C, linear terms p, quadratic terms q and homographic terms r, respectively, can be used.

The presence of quadratic and homographic terms enables better account to be taken of the synergics of the mixtures which, in the case of non-additive properties, are normal and which explain the non-application of the linear law of mixtures. These quadratic and homographic terms may or may not be used depending on the level of precision required.

In addition, the invention is intended not only for determining the properties of a blended products but to predict them from the components, by determining the corresponding spectral mixture indices SMI of the components of the blend.

In the case of a hydrocarbon component A, B or C, forming part of the mixture, the spectrum of the component alone can be obtained either by a line by line measurement provided for this component in the mixture M, or by a standardisation measurement of this spectrum if this component is a well defined and constant product.

The spectral mixture index is then obtained for the property J of the product A-$SMI^J_A$-by applying formula (2) above with the absorbances $D_i$ of the spectrum of A.

According to a preferred embodiment, the spectrum of a component A is preferably obtained by carrying out spectral measurements not on the pure product A but on an arbitrary mixture containing a fraction f, by volume, of A in a complementary fraction 1-f, by volume, of a matrix S, where f is between 0 and 1, preferably between 0.1 and 0.5.

The spectrum of the matrix S is then determined, in which S itself can be a mixture and which enables the determination of the absorbances $D_{im}$ at the frequencies $F_i$ selected, and also the spectrum of the previous arbitrary mixture which enables the corresponding absorbances $D_{im}$ at the frequencies $F_i$ selected, to be determined.

For each frequency $F_i$, a theoretical absorbance for the mixture $D_{ia}$ is calculated using the following expression:

$$D_{ia} = \frac{D_{im} - (1-f)D_{is}}{f} \quad (3)$$

Formula (2) is then applied to the values $D_{im}$ thus obtained, in order to obtain the spectral mixture index SMI of the ingredient A in the matrix S.

In the case of an oxygen containing additive, e.g. tertiary butyl alcohol, methyl tertiary butyl ether, methanol, or other alcohols, esters, ketones, phenols etc, the latter procedure is preferably used with a volume fraction of oxygenate between 0.02 and 0.15.

In the case of a nitrogen containing additive of the nitrate type, this last method is preferably used with an additive fraction between 0.02 and 0.15 by volume.

Once the spectral mixture index $SMI^J_I$ is obtained for each of the properties J of the ingredients I of a mixture, the properties of a new mixture can be determined by the simple application of a linear mixture law applied to these $SMI^J_I$ values.

For example, if a given motor spirit blend M of octane no. ON is to be altered by adding components A and B, whose respective volume fractions are defined as $F_a$ and $F_b$ respectively, the octane number ON' of the new blend M' thus obtained is expressed, as a function of the octane number ON of M, by the following formula:

$$ON'=ON.(1-f_a-f_b \ldots )+f_a \, SMI_a+f_b \, SMI_b$$

The fractions f may lie between 0 and 1, and preferably between 0 and 0.5.

If, on the other hand, a blend M is to be created from fractions $f_a$ of A, $f_b$ of B, $f_c$ of C . . . , $f_o$ of O, the octane number of the blend is obtained by the following formula:

$$ON=f_a.SMI_a+f_b.SMI_b+f_c.SMI_c \ldots +f_o.SMI_o$$

the fractions again lying between 0 and 1, and preferably between 0 and 0.5.

Alternatively, if it is required to modify the cloud point of a given gas oil mixture M by adding components such as A and B whose fractions by volume, respectively $F_a$ and $F_b$, are defined, the cloud point CP' of the new mixture M' thus obtained is expressed, as a function of the cloud point CP of M, by the following formula:

$$CP'=CP \, (1-F_a-f_b \ldots )+f_a \, SMI^{PT}_a+f_b \, SMI^{PT}_b \quad (4)$$

The fractions f may be between 0 and 1, preferably between 0 and 0.5.

In the reverse case where it is required to make up a mixture M from fractions $f_a$ of A, $f_b$ of B, $f_c$ of C ... $f_o$ of O, the cloud point of the mixture is obtained from the following formula:

$$CP = f_a \cdot SMI^{PT}_a + f_b \cdot SMI^{PT}_b + f_c \cdot SMI^{PT}_c \ldots + f_o \cdot SMI^{PT}_o \quad (5)$$

the fractions this time being between 0 and 1, preferably between 0 and 0.5.

The above method, used for the cloud point, can be used for other properties used in the formulation and characterisation of gas oils.

As a further example, if it is required to modify the viscosity at 100° C. of a given mixture M by adding components such as A and B whose fractions by volume, respectively $F_a$ and $F_b$, are defined, the viscosity at 100° C. V100' of the new mixture M' thus obtained is expressed, as a function of the viscosity V100 of M, by the following formula:

$$V100' = V100(1 - F_a - f_b \ldots) + f_a \, SMI^{V100}_a + f_b \, SMI^{V100}_b \quad$$

The fractions f may be between 0 and 1, preferably between 0 and 0.5.

In the reverse case where it is required to make up a mixture M from fractions $f_a$ of A, $f_b$ of B, $f_c$ of C ... $f_o$ of O, the viscosity of the mixture is obtained from the following formula:

$$V100 = f_a \cdot SMI_a + f_b \cdot SMI_b + f_c \cdot SMI_c \ldots + f_o$$

the fractions this time being between 0 and 1, preferably between 0 and 0.5.

The above method, used for viscosity, can be used for other properties, notably for the properties used for assessing the stability of the fuel:

PSR: solvent power of the residue corresponds to the ability of the residue R to keep its asphaltenes in solution.

PSFF solvent power of the flux F which defines the peptisation capacity of the flux vis-a-vis the asphaltenes.

CR: precipitation capacity of the asphaltenes of the residue R which can be defined in terms of initial precipitation capacity or precipitation capacity on storage.

The stability of the blended fuel is defined by:

$$S = \sum_{i=1}^{n} IPSR_i f R_i + \sum_{j=1}^{m} IPSF_j f F_i - \sum_{i=1}^{n} ICR_i \quad (6)$$

where: $f_{Ri}$, $f_{Ri}$ are the respective proportions of each of the ingredients, these being residues ($R_i$) or fluxes ($F_i$).

$IPSR_i$, $IPSF_j$ and $ICR_i$, represent the spectral mixture index for the solvent power of the residue, the solvent power of the flux, and the precipitation capacity of the asphaltenes respectively, for the compounds i and j. The fuel is stable if S is greater than O. The method can be put on-line and in real time by a process computer from sensors analysing in the NIR the spectra obtained from components which may originate from various sources. It is then possible to optimise the hydrocarbon mixture in real time.

It is possible, by a feedback control system on the unit providing each component, to affect the level of the desired property of this component, determined in real time, by analysis in the NIR, on-line, and calculating it by the computer by the method according to the invention.

In a computer assisted blending process, the NIR spectrum of the batches included is thus determined in real time, and is treated as an information vector continuously qualifying the potential properties of the feeds used in the mixing operation. The content of the NIR spectrum and the experimental accuracy deriving from the spectral information by fast Fourier transformation ensure that this information is reliable and relevant with respect to the operations involved in blending. The NIR spectrum is thus a numerical indication of the suitability of the products for blending operations.

According to another aspect of the present invention there is provided apparatus for carrying out a method for the determination of the physical properties of a hydrocarbon blend, the apparatus comprising an infra red spectrometer linked to a computer programmed in such manner that the property may be determined continuously and in real time.

The apparatus may comprise a feedback control system, for computer control of the blending equipment in response to variations of the property from the desired value, from the determination of the NIR spectrum of the components of the blend.

On-line analysis may use fibre optics as a means for transmitting light signals or may involve physical transference of a sample to the cell of the spectrometer.

In the following Examples it is shown that the variations in quality of the mixture formed can be correlated, by means of a numerical treatment, with the variations in the NIR spectra of the products.

Example 1

Alteration of the Octane Number of a given Blend to a Specification Imposed by Adding a Hydrocarbon Base The absorbancies measured are as follows:

| Frequency | Absorbance | |
|---|---|---|
| | Blend M (premium) | Component A (Hydrogenated Steam Cracking Gasoline) |
| $D_1$ 4670 cm$^{-1}$ | 0.0866 | 0.1455 |
| $D_2$ 4485 | 0.08040 | 0.07590 |
| $D_3$ 4332 | 0.75670 | 0.64380 |
| $D_4$ 4100 | 0.36810 | 0.36130 |
| $D_5$ 4060 | 0.55560 | 0.80420 |
| $D_6$ 4305 | 0.6290 | 0.55240 |
| $D_7$ 4210 | 0.36360 | 0.33350 |
| $RON_{0.4}$ Experimental engine | 98.9 | 100.3 |

The last line gives $RON_{0.4}$ which is the research octane number at 0.4% of tetraethyl lead measured experimentally by the engine method for M and A respectively.

The octane number is calculated by means of the following formula derived from equation (2) and obtained using multivariate numerical analysis techniques applied to a set of blends M serving for prior calibration.

$$RON_{0.4} = 93.29 - 28.46 \, D_1 - 47.19 \, D_5 D_6 + 42.78 \, D_3 - 60.64 \, D_4 + 60.40 \, D_5 - 52.05 \, D_7 \quad (7)$$

This formula applied to blend M gives the value of $RON_{0.4} = 99.0$.

The SMI of component A is also calculated by means of equation (7), and the result is:

$SMI_1 = 105.0$.

It will be noted that this value is higher than that of 100.3 in the preceding table, showing the bonus effect of A in a blend with M.

Thus, by adding 20% volume of A to M, a calculated $RON_{0.4}$ is obtained for blend $M'=0.2A+0.8M$ of $RON_m$: $0.2\times 105+0.8\times 99\times 100.2$, whereas experimentally the engine test gives 100.1.

With a blend having 10% volume of A, the same calculation gives 99.6 in comparison to an engine measurement of 99.3.

Example 2

Production of a Motor Spirit Involving a Ternary Blend

The absorbances are detected at the same frequencies as those in Example 1.

| Blend M | Absorbance | |
|---|---|---|
| | Component B (Gasoline) | Component C (Fluidised Bed Catalytic Cracker Gasoline) FCC |
| $D_1$: 0.0866 | 0.0109 | 0.04770 |
| $D_2$: 0.08040 | 0.03840 | 0.06950 |
| $D_3$: 0.75670 | 0.96970 | 0.8520 |
| $D_4$: 0.36810 | 0.58420 | 0.40180 |
| $D_5$: 0.55560 | 0.36920 | 0.55140 |
| $D_6$: 0.6290 | 0.6838 | 0.73460 |
| $D_7$: 0.3636 | 0.4959 | 0.44870 |
| $RON_{0.4}$ 98.9 engine | 83.5 | 94.5 |
| $RON_{0.4}$ 98.9 engine SMI 99.0 (Calculated by equation (7) in Example 1) | 83.6 | 94.9 |
| | (no synergy in blend) | (slight bonus effect) |

The ternary blend formed of:

70% volume M

15% volume B

15% volume C has an experimental engine $RON_{0.4}$ of $RON_{0.4}$ engine=96.2, whereas the calculated value gives: RON calculated=$0.7\times 99+0.15\times 83.6+0.15\times 94.9=96.1$.

Here too, the agreement is satisfactory and the spectral method offers the possibility of calculating a complex blend without having to use blend tables, which are difficult to compile to cover all possible cases.

This procedure is applicable whatever the number of components in the blend.

Example 3

A Blend Involving Methyl Tertbutyl Ether MTBE

An arbitrary blend of 0.15 MTBE in 0.85 matrix S (motor spirit) was produced.

The absorbances for the matrix S and this particular blend respectively are shown in the first two columns of the table below:

The absorbances are detected at the same frequencies as those in Example 1.

| | Absorbance | |
|---|---|---|
| Motor Spirit S | 0.85 S + 0.15 MTBE | MTBE in blend |
| $D_1$: 0.06286 | 0.05343 | 0.0000 |
| $D_2$: 0.07794 | 0.07979 | 0.09027 |
| $D_3$: 0.80927 | 0.88224 | 1.29574 |
| $D_4$: 0.37732 | 0.38817 | 0.44965 |
| $D_5$: 0.53719 | 0.52851 | 0.47932 |
| $D_6$: 0.68849 | 0.65069 | 0.43649 |
| $D_7$: 0.40019 | 0.42958 | 0.59612 |

The third column in the table corresponds to the tepretical spectra of MTBE in matrix S obtained by applying, for each of the seven frequencies, formula (3) above with f=0.15. Thus, $$D_{ia} = \frac{D_{im} - 0.85 D_{is}}{0.15} \quad (8)$$

From the theoretical spectrum shown in the right hand column, calculated from formula (8), and by applying formula (7), the SMI of MTBE may be deduced in relation to matrix S.

$SMI_{MTBE}=110.1$

It is then possible to calculate the various blends of S+MTBE or S+MTBE+X.

Thus, 10% of MTBE combined with S give an octane number calculated according to the invention having the following values:

Blend S:

RON engine=97.1

RON calc.=97.4

Blend of 10% MTBE in S:

RON engine=98.6

RON calc.=$0.1\times 110.1+0.9\times 97.4=98.67$

Blend of 5% MTBE in S:

RON engine=97.9

RON calc.=$0.05\times 110.1+0.95\times 97.4=98.04$

Example 4

A Ternary Blend Containing an Oxygenate

The procedure according to the invention is also capable of dealing with ternary blends involving an oxygenate.

Thus, blend X, formed of: $X=0.7(S)+0.1(MTBE)+0.2(A)$ where component A is that of Example 1, was measured in the engine by two successive measurements which yielded research octane numbers of 99.9 and 100.2 respectively.

The calculation using the procedure according to the invention gives: $0.7\times 97.1+0.1\times 110.1+0.2\times 105=99.98$ which value lies between the two engine measurements.

Example 5

Formulating a Motor Spirit

The procedure according to the invention is applied to produce a motor spirit from different hydrocarbon bases.

In the example, four bases are used:

$B_1$=a fluidised bed catalytic cracker gasoline $B_2$=a reformate $B_3$=an atmospheric distillation gasoline $B_4$=a steam cracker gasoline.

The absorbency values obtained at the same frequencies as before are as follows:

| Absorbance | | | | |
|---|---|---|---|---|
| | $B_1$ | $B_2$ | $B_3$ | $B_4$ |
| $D_1$ | 0.0475 | 0.0877 | 0.0109 | 0.1972 |
| $D_2$ | 0.0681 | 0.0488 | 0.0384 | 0.0682 |
| $D_3$ | 0.8471 | 0.7541 | 0.9697 | 0.5278 |
| $D_4$ | 0.3791 | 0.3614 | 0.5842 | 0.3252 |
| $D_5$ | 0.5360 | 0.5923 | 0.3692 | 0.8941 |
| $D_6$ | 0.7275 | 0.6238 | 0.6838 | 0.4736 |
| $D_7$ | 0.4327 | 0.3745 | 0.4958 | 0.2966 |
| $RON_{0.4}$ | 95.3 | 98.8 | 83.5 | 101.4 |
| SMI | 96.6 | 100 | 83.6 | 109 |

For a blend M with the following proportions by volume:

35% $B_1$

10% $B_2$

30% $B_3$

25% $B_4$ using the procedure according to the invention, a research octane number of 96.16 is obtained, which may be compared to the experimental values of 96 and 96.2.

For a blend M' with the following proportions by volume:

30% $B_1$

10% $B_2$

40% $B_3$

20% $B_4$ a calculated value of 94.24 is obtained in comparison to experimental values of 94.2 and 94.5.

Example 6

The cetane value of a gas oil is determined from absorbance measurements obtained from the NIR spectrum of the components of the mixture.

The four components of the mixture have the following characteristics:

A: gas oil obtained from the atmospheric distillation of a crude oil:
  cetane index: 50.9
  density at 15° C.: 0.8615

B: light gas oil obtained from a fluidised bed catalytic cracking unit:
  cetane index: 25.7
  density at 15° C.: 0.9244

C: premix of various ingredients:
  cetane index: 48.7
  density at 15° C.: 0.8487

D: visbroken light gas oil:
  cetane index: 45.8
  density at 15° C.: 0.8587

The cetane index was determined by the standard method ASTM D976.

The spectroscopic measurements carried out on each of the components of the mixture, and on a mixture containing the following proportions by volume of each of the components: 20% of A, 30% of B, 40% of C, 10% of D, give the following results for the four frequencies used:

| | Absorbance | | | |
|---|---|---|---|---|
| Frequencies in $cm^{-1}$ | Component A | Component B | Component C | Component D |
| $F_1 = 4640$ | $D_1 = 0.02211$ | $D_1 = 0.08097$ | $D_1 = 0.02229$ | $D_1 = 0.0241$ |
| $F_2 = 4485$ | $D_2 = 0.04270$ | $D_2 = 0.07896$ | $D_2 = 0.04282$ | $D_2 = 0.05629$ |
| $F_3 = 4260$ | $D_3 = 0.80297$ | $D_3 = 0.58219$ | $D_3 = 0.78483$ | $D_3 = 0.76965$ |
| $F_4 = 4135$ | $D_4 = 0.53053$ | $D_4 = 0.36406$ | $D_4 = 0.51901$ | $D_4 = 0.49267$ |
| Measured cetane index | 50.9 | 25.7 | 48.7 | 45.8 |
| SMI | 50.2 | 14.6 | 48.9 | 45.1 |

The SMI is the spectral mixture index of the ingredient considered for the cetane index.

It is obtained from an expression of type (2) which, in the case of the cetane index is:

$$SMI = 25.0093 - 182.349\, D_1 - 437.405\, D_2 + 193.148\, D_3 - 202.099\, D_4 \quad (9)$$

The linear combination of the SMI according to the proportions of the various components, according to an equation of type (5), gives the following expression:

Cetane index calculated for the mixture, $$(0.2 \times 50.2) + (0.3 \times 14.6) + (0.4 \times 48.9) + (0.1 \times 45.1) = 38.5$$

The cetane index of the mixture determined according to the standard method is 38.3.

Example 7

As in Example 6 the cetane index of a mixture is calculated from the NIR spectrum of the components:

A: visbroken light gas oil:
  cetane index: 45.7
  density: 0.8587

B: heavy gas oil from a fluidised bed catalytic cracking unit:
  cetane index: 28.2
  density: 0.9731

C: premix of gas oils:
  cetane index: 48.8
  density: 0.8487

The spectroscopic measurements carried out on each of the components on a mixture consisting of equal volume of each component give the following results:

| | Absorbance | | |
|---|---|---|---|
| Frequencies in $cm^{-1}$ | Component A | Component B | Component C |
| $F_1 = 4640$ | 0.0241 | 0.08111 | 0.02229 |
| $F_2 = 4485$ | 0.05629 | 0.07515 | 0.04282 |
| $F_3 = 4260$ | 0.76965 | 0.61857 | 0.78483 |
| $F_4 = 4135$ | 0.49267 | 0.40121 | 0.51901 |
| Measured cetane index | 45.7 | 28.2 | 48.7 |
| SMI | 45.1 | 15.7 | 48.9 |

The SMI of each component is obtained from equation (9). The cetane index (CI) of the mixture is obtained from the expression linking the SMI values and the proportion of each component in this mixture:

$CI=(\frac{1}{3} 45.1)+(\frac{1}{3} 15.7)+(\frac{1}{3} 48.9)$ i.e. 36.5. The cetane index of the mixture determined by the standard method is 37.0.

Example 8

The cloud point of a gas oil is determined from absorbance measurements carried out by NIR spectroscopy on the components of the mixture.

The components of the mixture have the following properties:

A: heavy gas oil from a fluidised bed catalytic cracking unit:
cloud point: +4° C.
B: light gas oil from a crude oil atmospheric distillation unit:
cloud point: −20° C.
C: gas oil from a vacuum distillation unit:
cloud point: +15° C.

The mixture consists of 20% by volume of A, 50% of B and 30% of C.

The absorbance of each of the ingredients and of the mixture are determined at the sixteen frequencies shown below.

The SMI corresponding to the cloud point (CP) is calculated from the following expression:

$SMI\ (CP)=-35.98+270.495\ D4210-124.16\ D4135-98.78\ D4100$

| Frequencies | Absorbance | | |
|---|---|---|---|
| in cm$^{-1}$ | A | B | C |
| $F_1$ 4670 | 0.05230 | 0.01689 | 0.01522 |
| $F_2$ 4640 | 0.08731 | 0.0264 | 0.02803 |
| $F_3$ 4615 | 0.0987 | 0.0354 | 0.03562 |
| $F_4$ 4585 | 0.08897 | 0.03576 | 0.03461 |
| $F_5$ 4485 | 0.0781 | 0.04582 | 0.0461 |
| $F_6$ 4385 | 0.44065 | 0.48046 | 0.4648 |
| $F_7$ 4332 | 0.77412 | 0.95276 | 0.94117 |
| $F_8$ 4305 | 0.61996 | 0.65619 | 0.64443 |
| $F_9$ 4260 | 0.59625 | 0.78596 | 0.78001 |
| $F_{10}$ 4210 | 0.4214 | 0.5382 | 0.53771 |
| $F_{11}$ 4170 | 0.42882 | 0.56386 | 0.56222 |
| $F_{12}$ 4135 | 0.38635 | 0.51699 | 0.51842 |
| $F_{13}$ 4100 | 0.37511 | 0.49663 | 0.49375 |
| $F_{14}$ 4060 | 0.44674 | 0.54552 | 0.53138 |
| $F_{15}$ 4040 | 0.35102 | 0.42414 | 0.41762 |
| $F_{16}$ 4405 | 0.35392 | 0.37502 | 0.35613 |
| Measured cloud point | +4° C. | −20° C. | +15° C. |
| SMI | −7 | −3.6 | −3.7 |

The cloud point of the mixture is obtained from the SMI values of the ingredients using the expression:

Cloud Point=0.2×(−7)+0.5 (−3.6)+0.3 (−3.7)=−4.3° C.

The cloud point of the mixture, measured according to the standard NFT 60105 is −4° C.

Example 9

A fuel oil was formulated from a residue mixture obtained from the visbreaking of an Arabian Heavy feed and a flux F1 (gas oil obtained by distillation at atmospheric pressure). The characteristics of the visbroken oil are as follows: density 1.0801, viscosity 500 cSt at 125° C.

The mixture is prepared in the following proportions: 60% by vol of residue (ingredient A) and 40% of flux (ingredient B).

The spectra of the products give the following values for the absorbances:

| Frequencies | Absorbance | |
|---|---|---|
| in cm$^{-1}$ | Component A | Component B |
| $F_1$ 4670 | 0.00876 | 0.01109 |
| $F_2$ 4640 | 0.02443 | 0.02091 |
| $F_3$ 4615 | 0.03194 | 0.02669 |
| $F_4$ 4585 | 0.03234 | 0.02731 |
| $F_5$ 4485 | 0.02736 | 0.04104 |
| $F_6$ 4385 | 0.29355 | 0.46874 |
| $F_7$ 4332 | 0.58201 | 0.96016 |
| $F_8$ 4305 | 0.40189 | 0.65164 |
| $F_9$ 4260 | 0.45314 | 0.80883 |
| $F_{10}$ 4210 | 0.29417 | 0.55592 |
| $F_{11}$ 4170 | 0.2807 | 0.58335 |
| $F_{12}$ 4135 | 0.24544 | 0.53974 |
| $F_{13}$ 4100 | 0.20957 | 0.51335 |
| $F_{14}$ 4060 | 0.24392 | 0.5507 |
| $F_{15}$ 4040 | 0.17575 | 0.43174 |
| $F_{16}$ 4405 | 0.21313 | 0.35756 |

The spectral mixture index of the solvent power of the IPSR residue is determined using the following expression:

$$IPSR=315.37+1823\ D_1-1676.95\ D_3-432.65\ D_7+370\ D_{15} \quad (10)$$

where: $D_1$ is the absorbance at the frequencies $F_1$ considered.

The mixture index of the solvent power obtained for component A is 104.8.

The spectral mixture index of the solvent power of the flux (IPSF) is determined using the following equation (11):

$$\begin{aligned}IPSF =\ & 218.59 + 548.31\ D_2 - 1104.74\ D_3 + \\ & 470.06\ D_4 - 50.65\ D_5 - 26.26\ D_5 - \\ & 77.65\ D_9 - 165.56\ D_{10} - 959.48\ D_{11} - \\ & 351.95\ D_{12} + 1042\ D_{13} + 487.7\ D_{14} - \\ & 378.2\ D_{15} - 2011.4\ D_{13} \cdot D_{14} + \\ & 905.5\ D_{10} \cdot D_{13} + 1285.5\ D_{10} \cdot D_{14} + \\ & 1500.8\ D_3 \cdot D_{10}\end{aligned}$$

The mixture index of the solvent power obtained for component B according to equation (11) is 41.1.

The spectral mixture index of the precipitation capacity of the residue (ICR) is determined from equation (12):

$$ICR=339.35+845.7\ D_1-432.65\ D_7 \quad (12)$$

The mixture index of the precipitation capacity of the residue (component A) determined from equation (12) is 94.9.

Calculation of the stability of the fuel obtained according to equation (6) gives S=−15.6.

The resulting fuel will not be stable as is confirmed experimentally by the HFT test carried out on the final product.

Example 10

A fuel is to be formulated from the components used in Example 9 and from a supplementary flux $F_2$ (a heavy gas oil obtained from a fluidised bed catalytic cracking unit.

The absorbance figures for the frequencies considered are given below for this new component:

| Frequencies in cm$^{-1}$ | Absorbance Flux F$_2$ Component C | Frequencies in cm$^{-1}$ | Absorbance Flux F$_2$ Component C |
|---|---|---|---|
| F$_1$ 4670 | 0.06646 | F$_9$ 4260 | 0.52437 |
| F$_2$ 4640 | 0.11133 | F$_{10}$ 4210 | 0.37553 |
| F$_3$ 4615 | 0.12978 | F$_{11}$ 4170 | 0.37963 |
| F$_4$ 4585 | 0.11513 | F$_{12}$ 4135 | 0.33693 |
| F$_5$ 4485 | 0.09335 | F$_{13}$ 4100 | 0.33919 |
| F$_6$ 4385 | 0.45794 | F$_{14}$ 4060 | 0.43509 |
| F$_7$ 4332 | 0.7056 | F$_{15}$ 4040 | 0.33422 |
| F$_8$ 4305 | 0.63896 | F$_{16}$ 4405 | 0.37942 |

The mixture proportions are as follows:

Component A-residue: 60% by volume

Component B-flux F$_1$: 30% by volume

Component C-flux F$_2$: 10% by volume

The following characteristics are determined from the equations given in Example 9:

IPSR (mixture index of the solvent power of residue A)=104.8 (equation 10)

ICR (mixture index of the precipitation capacity of the residue A)=94.8 (equation 12)

IPSF$_1$ (mixture index of the solvent power of the flux F$_1$-component B)=41.1 (equation 11)

IPSF$_2$ (mixture index of the solvent power of the flux F$_2$-component C)=128.8 (equation 11)

Calculation of the stability of the fuel using equation (6) gives S=−6.7.

The instability of the fuel obtained by mixing components A, B and C in the proportions indicated is confirmed by the result of the HFT test which shows that the resulting product is outside the specification.

The proportion of flux F$_2$ to be used in order to obtain a stable final product can be determined from the following equations:

$$\left. \begin{array}{l} \text{Expression } (S) \text{ with } \quad f_R = 0.6 \\ \qquad\qquad\qquad f_{F1} + f_{F2} = 0.4 \\ \qquad\qquad\qquad S \text{ greater than } 0 \end{array} \right\}$$

we obtain: f$_{F2}$ greater than 17.8%

The stability calculated for a mixture containing 18% of the flux F$_2$ gives S=+0.2.

Experimental verification by the HFT test and the optical microscope is satisfactory.

Example 11

The proportions to be mixed in order to obtain a product of viscosity determined from spectroscopic data obtained by analysis of the components of the mixture are to be calculated.

A residue (component D) is used, the properties of which are as follows:

density=1.036 viscosity at 100° C.=598 cSt

This is mixed with the flux F$_2$ of Example 10 (ingredient C) in order to obtain a fuel with a viscosity of 80 cSt at 100° C.

The spectrum of the component D gives the following values:

| Frequencies in cm$^{-1}$ | Absorbance Residue Component D | Frequencies in cm$^{-1}$ | Absorbance Residue Component D |
|---|---|---|---|
| F$_1$ 4670 | 0.01284 | F$_9$ 4260 | 0.51767 |
| F$_2$ 4640 | 0.03023 | F$_{10}$ 4210 | 0.34506 |
| F$_3$ 4615 | 0.03825 | F$_{11}$ 4170 | 0.33794 |
| F$_4$ 4585 | 0.03767 | F$_{12}$ 4135 | 0.30178 |
| F$_5$ 4485 | 0.03565 | F$_{13}$ 4100 | 0.26383 |
| F$_6$ 4385 | 0.32445 | F$_{14}$ 4060 | 0.29733 |
| F$_7$ 4332 | 0.63721 | F$_{15}$ 4040 | 0.22409 |
| F$_8$ 4305 | 0.45729 | F$_{16}$ 4405 | 0.22774 |

The proportions of the components D and of the flux F$_2$ can be determined using the following equations in which SMI (V100)$_R$ and SMI (V100)$_F$ denote the spectral mixture index for the viscosity at 100° C., the residue and the flux, respectively obtained from:

$$SMI\ (V100)_i = 1031.04 - 4175.9\ D_1 + 9201.6\ D_4 - 4074.7\ D_{14} \tag{13}$$

$$f_R + f_{F2} = 1 \tag{14}$$

$$SMI\ (V100)_R f_R + SMI\ (V100)_F f_F = 80 \tag{15}$$

Equation (13) gives:

$$SMI\ (V100)_R = 112.5 \quad SMI\ (V100)_F = 40$$

From equations (14) and (15) we obtain:

f$_R$=55.5% f$_F$=44.5%

The experimental verification gives a viscosity of 79.8 cSt if the residue and the flux are mixed in the proportions calculated for a required viscosity of 80 cSt.

We claim:

1. A method for preparing a blend of liquid hydrocarbon components and controlling at least one physical property of the blend, the method comprising the following steps:

(a) determining with an IR spectrometer, an absorbance at each of a selected number of frequencies in a spectral range 16667 to 3840 cm$^{-1}$ for each component starting from a defined base line, (b) determining for each component I and each physical property J, a spectral mixture index (SMI)$^J_I$ by applying a correlation with measured absorbance values, wherein the correlation is determined experimentally by multivariate regression of a set of blends serving for calibration and is dependent upon the spectrometer used, the property selected and the frequencies used, (c) selecting one or more physical properties desired in the blend, (d) calculating for the selected property J of the blend the quantity of the components required to obtain such physical property by applying a linear expression:

$$J = f_a \cdot SMI^J_a + f_b \cdot SMI^J_b + f_c \cdot SMI^J_c \ldots + f_o \cdot SMI^J_o \tag{1}$$

each term of which is a product of the spectral mixture index (SMI$_a$ ... ) of the property J for a component (A ... ) and a fraction by volume (f$_a$ ... ) of this component, and (e) mixing the calculated quantities of the components to obtain the desired blend.

2. The method according to claim 1 wherein the frequencies are in the spectral range 12500 to 3840 cm$^{-1}$.

3. The method according to claim 2 wherein the frequencies are in the spectral range 4760 to 4000 cm$^{-1}$.

4. The method according to claim 3 wherein the frequencies used are selected from the following list:
4670 cm$^{-1}$
4640 cm$^{-1}$
4615 cm$^{-1}$
4585 cm$^{-1}$
4485 cm$^{-1}$
4405 cm$^{-1}$
4385 cm$^{-1}$
4332 cm$^{-1}$
4305 cm$^{-1}$
4260 cm$^{-1}$
4210 cm$^{-1}$
4170 cm$^{-1}$
4135 cm$^{-1}$
4100 cm$^{-1}$
4060 cm$^{-1}$ and
4040 cm$^{-1}$.

5. The method according to claim 1, wherein the base line is taken as 4780 cm$^{-1}$.

6. The method according to claim 1 wherein the spectrometer is linked to a signal processing device to permit numerical treatment of the spectrum.

7. The method according to claim 6 wherein the numerical treatment is by Fourier transformation.

8. The method according to claim 1 wherein the method is on-line and in real time.

9. The method according to claim 1 wherein the properties calculated are non-additive properties of the components.

10. The method according to claim 1 wherein the liquid hydrocarbon blend additionally contains a liquid organic additive.

11. The method according to claim 1 wherein the product is a motor spirit and the property determined is selected from at least one of research and motor octane numbers (clear and leaded), product density, product vapor pressure and product distillation characteristics.

12. The method according to claim 11 wherein the frequencies are selected from the following:
4670 cm$^{-1}$
4485 cm$^{-1}$
4332 cm$^{-1}$
4305 cm$^{-1}$
4210 cm$^{-1}$
4100 cm$^{-1}$ and
4060 cm$^{-1}$.

13. The method according to claim 1 wherein the product is a diesel oil and the property determined is selected from the following: cloud point, pour point, filterability, cetane index, distillation characteristics, flash point and viscosity.

14. The method according to claim 1 wherein the product is a fuel oil and the property determined is selected from the following: density, viscosity, thermal stability, distillation characteristics and flash point.

15. The method of claim 1 wherein blending equipment is used to produce the blend of liquid hydrocarbon components and said blending equipment is computer controlled by a feedback control system for altering the fraction by volume of each component in the blend in response to variations from a desired value for a property of the blend.

16. A method according to claim 1 wherein the physical property is any one of octane number, research octane number, motor octane number, cloud point, flash point, pour point, cetane index, filterability, viscosity, density, vapor pressure, distillation characteristic, thermal stability, solvent power, and precipitation capacity.

17. A method according to claim 1 wherein the spectral mixture index of a property of a component is determined directly from absorbances obtained for said component alone.

18. A method according to claim 1 wherein the spectral mixture index of a property of a component is determined from the theoretical absorbance of said component by preparing an arbitrary mixture with a fraction of said component in a matrix, determining the NIR spectra for the matrix and the mixture, respectively, and calculating a theoretical absorbance.

* * * * *

UNITED STATES PATENT AND TRADEMARK OFFICE
CERTIFICATE OF CORRECTION

PATENT NO. : 5,475,612
DATED : December 12, 1995
INVENTOR(S) : ALAIN ESPINOSA, DIDIER C. LAMBERT, ANDREW MARTENS, ANTOINE PASQUIER and GILBERT VENTRON It is certified that error appears in the above-indentified patent and that said Letters Patent is hereby corrected as shown below:

Col. 2, l. 11, the word "However" should start a new paragraph

Col. 3, l. 54, correct the spelling of the word "synergi$\underline{e}$s"

Col. 5, l. 20, in the equation the designation should be "SMI V100"

Col. 5, l. 29, in the equation, replace "$f_o$" with -- + $f_0 \cdot SMI$ --

Col. 5, l. 56, "The method can be" should start a new paragraph

Col. 7, l. 5, after "$RON_m$" and before "0.2" insert an equal "=" sign

Col. 7, l. 6, after "99", strike the multiplication sign "x" and insert an equal "=" sign therefor Col. 10, l. 23, the last number should read "-202.099 $D_4$"

Signed and Sealed this

Twenty-third Day of April, 1996

Attest:

BRUCE LEHMAN

*Attesting Officer*  *Commissioner of Patents and Trademarks*